United States Patent [19]

Cooper

[11] 4,255,439

[45] Mar. 10, 1981

[54] MEANS AND METHOD FOR AIDING INDIVIDUALS TO STOP SMOKING

[76] Inventor: Irving Cooper, 20 Westgate Rd., Newton Centre, Mass. 02159

[21] Appl. No.: 57,288

[22] Filed: Jul. 13, 1979

[51] Int. Cl.$^3$ .............................................. A61K 31/415
[52] U.S. Cl. ............................... 424/273 R; 424/248.4
[58] Field of Search ........................ 424/273 R, 248.4

[56] References Cited

U.S. PATENT DOCUMENTS

| 3,146,240 | 8/1964 | Hageman et al. | 424/273 R |
|---|---|---|---|
| 3,236,857 | 2/1966 | Zeile et al. | 424/273 R |
| 3,850,926 | 11/1974 | Stähle et al. | 424/273 R |
| 4,025,607 | 5/1977 | Stähle et al. | 424/273 R |
| 4,100,292 | 7/1978 | Stähle et al. | 424/273 R |

FOREIGN PATENT DOCUMENTS

759125 5/1971 Belgium .............................. 424/273 R

OTHER PUBLICATIONS

Chem. Abst. 77,122267(c) (1972)–Le Douarec et al.

*Primary Examiner*—Douglas W. Robinson
*Attorney, Agent, or Firm*—Wolf, Greenfield & Sacks

[57] ABSTRACT

Individuals are aided in their desire to stop tobacco smoking and lose overweight by administering internally a combination of pharmaceuticals comprising an imidazoline derivative, such as clonidine hydrochloride, with an anorectic, such as phentermine resin.

14 Claims, No Drawings

MEANS AND METHOD FOR AIDING INDIVIDUALS TO STOP SMOKING

BACKGROUND OF THE INVENTION

It is estimated that there are over 54,000,000 persons in the United States seventeen years or older who smoke tobacco in the form of cigarettes, cigars, or via pipes. The hazards of tobacco smoking due to coal tars, carbon monoxide, and nicotine are now well-known. Tobacco use leads to physiological addiction and/or psychological dependence. Many of these persons are also overweight.

Even social tobacco smoking of two or more cigarettes is often followed by an escalation to where people become addicted and/or psychologically dependent. This includes use of cigars and pipes.

A large variety of methods and apparatus have been used to stop people from tobacco smoking. These range from psychological to chemical approaches. However, the nicotine withdrawal syndrome and/or weight gain and/or the pleasures missed such as taste are so severe that no one method or any combinations of methods have been successful to stop many millions of tobacco smokers from continuing.

The difficulties inherent in ending the use of tobacco and its nicotine content in almost all cases are (a) nicotine withdrawal syndrome appear such as increased tension, irritability, restlessness, intense craving, depression, bradycardia, hypotension, constipation, sleep disturbance, EEG changes, hypoglycemia, hypocalcemia, decreased oxygen consumption and/or (b) increase in body weight and/or (c) the pleasures missed such as taste.

SUMMARY OF THE INVENTION

It is an object of this invention to provide a method for individuals in stopping their nicotine addiction and/or psychological dependence due to tobacco and preferably to lose overweight if any with the use of administration of a combination of pharmaceuticals including an imidazoline derivative and an anorectic.

It is a still further object of this invention to provide a method in accordance with the preceding object wherein the imidazoline derivative is clonidine hydrochloride.

Still another object of this invention is to provide a combination of drugs for aiding individuals to stop their nicotine addiction and/or psychological addiction and/or lose overweight if any which combination comprises an imidazoline derivative preferably clonidine hydrochloride and an anorectic preferably phentermine resin.

According to the invention a method of aiding individuals to stop smoking and lose overweight if any comprises administering a combination of pharmaceuticals to the individuals which combination comprises an imidazoline derivative and an anorectic. The imidazoline derivative has a mechanism of action which appears to be a central α adrenergic stimulation that results in the inhibition of bulbar sympathetic cardioaccelerator and sympathetic vasoconstrictor centers thereby causing a decrease in sympathetic outflow from the brain. The imidazoline derivative preferably has at least three actions which are drying the mouth, calming the subject and distorting the tobacco smoke taste. This agent is preferably clonidine hydrochloride and the anorectic is preferably phentermine resin.

Preferably the drugs are administered over a time span of several weeks and the dosages of each drug is titrated to the human patient to obtain the desired results with the maximum of effectiveness and safety.

It is a feature of this invention that the use of the pharmaceuticals enables people to stop smoking tobacco over a relatively reasonable time period of about a month or sooner while remaining calm, whereas with different methods people often fail to stop smoking due to the unbearable nicotine withdrawal syndrome. People, who have previously gained weight while attempting to stop tobacco smoking with other methods, are motivated when they are aware that not only do they not gain weight but lose overweight. The pleasures experienced in the past of tobacco smoking become unpleasant because of distorted taste. Some patients make statements such as "Cigarettes taste like garbage, rotten eggs, bitter, etc.".

DESCRIPTION OF PREFERRED EMBODIMENTS

While the exact action of nicotine and the drugs of this invention is not known, it is theorized the nicotine molecule is a ganglionic stimulating drug affecting both specific receptor sympathetic and parasympathetic ganglia. Small dosages of nicotine will stimulate these specific receptor ganglia to release neurotransmitters such as noradrenalin and acetycholine; however, larger doses of nicotine depress these specific receptor cells and the neurotransmitters are blockaded. As a result the more specific neuroeffector cells involved, the greater the dosage of nicotine that can be tolerated since less and less specific receptor sympathetic and parasympathetic ganglia remain to be stimulated.

The physiological functions of the body now adapt to this new status which is dependent upon the continuous intake of nicotine. When nicotine is withdrawn then the blockade of the neurotransmitters noradrenalin and acetylcholine is lifted and the nicotine withdrawal syndrome occurs.

It is believed that tolerance and addiction as described above occurs only in those people who have a nicotine receptor protein in their ganglia that causes the addiction. Those people who do not have nicotine receptor protein in their cells do not become addicted but are psychologically dependent upon tobacco smoking.

Many people are unable to stop tobacco smoking due to nicotine withdrawal syndrome, fear of weight gain, psychological pleasure due to taste, relief of stress, etc. These conditions in certain patients who are physiologically addicted and/or psychologically dependent can be helped.

Clonidine hydrochloride drys the mouth, alters the smoke taste and relieves chronic stress while phentermine resin acts as an anorectic. This combination of drugs reduces drastically withdrawal symptoms, acts to prevent weight gain and promotes weight loss, and alters taste so that tobacco taste becomes obnoxious. In one week, smell and taste return to the individual so that people smoking around them reinforce the aversion behavioral reflex.

The imidazoline derivative which acts as a central α adrenergic stimulator that results in the inhibition of bulbar sympathetic cardio-accelerator and sympathetic vasoconstrictor centers thereby causing a decrease in sympathetic outflow from the brain, is preferably clonidine hydrochloride which is 2-(2,6-dichlorophenylamino)-2-imidazoline hydrochloride. Clonidine hydrochloride is known for use in blood pressure management. The drug purportedly has been used to control narcotic addiction in certain individuals. Clonidine hydrochloride has the following structural formula:

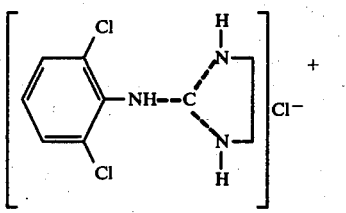

It is an odorless, bitter white crystalline substance soluble in water and alcohol with a molecular weight of 266.57. It is available in tablet form under the trade name "Catapres", a brand of Boehringer Ingelheim Ltd. of Ridgefield, CT. Liquid solutions can also be used by injection although oral ingestion of the combination of drugs of this invention is preferred. Other derivatives of clonidine having the desired properties should be considered included in the terminology "clonidine hydrochloride".

The imidazoline derivative can be a 2 imidazoline having the formula

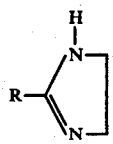

and R is such that the resulting derivative is preferably one of naphazoline, tetrahydrazoline, oxymetazoline, xylometazoline, tolazoline, and antazoline.

In the treatment of this invention, clonidine hydrochloride is preferably used in dosages which can vary depending upon the individual although doses of from 0.05 to 2.4 milligrams daily are possible and perhaps higher. In most cases, a dosage of from 0.05 mgs two times a day (b.i.d.) to 0.1 milligrams four times a day (q.i.d.) for four weeks along with the anorectic used is sufficient to obtain the smoking inhibition desired. When other 2-imidazoline derivatives are used in combination with each other and clonidine or in place of clonidine they are used in dosages that are safe and effective.

The anorectics which could be used in the present invention include the following:
  phentermine resin
  chlorophentermine
  fenfluramine
  benzphetamine
  phenmetrazine
  phendimetrozine
  diethylpropion
  phenylpropanolomine Phentermine resin is particularly suitable for use in combination with clonidine hydrochloride. Phentermine is α, α-dimethyl phenylethylamine and is an anorectic. It does suppress appetite but also has central nervous system actions which appear to give a compatible effect with clonidine hydrochloride in aiding individuals to stop the use of nicotine and particularly tobacco smoking. The drug helps suppress appetite during withdrawal of nicotine and also to alleviate fatigue. It coacts with the clonidine hydrochloride to overcome the nicotine withdrawal syndrome and weight gain, and aids in loss of overweight, and distorting taste.

Preferably phentermine resin is used in amounts of from 15 to 30 milligrams daily for a period of one month with the clonidine hydrochloride. Both the dosage of the anorectic and the 2-imidazole derivative can be adjusted to vary the rate, depending upon the reaction of the individual to the drugs. Phentermine resin is available as Ionamin, a trademarked product of Pennwalt Corporation of Rochester, N.Y. and is an α, α-dimethyl phenylethylamine (phenyl-tertiary-butylamine).

The program to enable one to stop smoking tobacco containing nicotine is preferably a one-month program although the time limit can vary. It challenges those patients who have tried to stop smoking by self-determination, group therapy (behavioral modification), hypnosis, acupuncture, psychotherapy and have failed due to withdrawal symptoms that they could just not endure, often along with unacceptable weight gain.

The program is limited to one month in order to maintain the drug usage for only a short period although it could be continued or reinstituted after the one-month period if required.

The following are examples of uses on patients of the drug combination of this invention following the method of this invention.

EXAMPLE I

A patient who had been advised to stop smoking due to coronary infarction one year before was treated. At the time he had been smoking twenty to thirty cigarettes a day. On the first visit, the patient orally ingested 0.1 milligrams of clonidine at night and the next day ingested phentermine resin in a 15 milligram tablet before breakfast. Clonidine hydrochloride was taken at 0.1 milligrams after breakfast. Clonidine was continued at 0.1 mg. b.i.d. and phentermine resin was continued b.i.d. The patient felt a dryness of mouth and stated that the taste of cigarettes was bad. He stopped smoking on the second day and did not smoke another cigarette during the one-month period of administration of the drug combination stating that he feels great. The patient was also placed on a thousand calorie diet and lost weight.

EXAMPLE II

A patient who had been in the hospital for emphysema went back to cigarette smoking because he could not endure withdrawal symptoms. The patient was given phentermine resin 15 milligrams once a day before breakfast and clonidine hydrochloride 0.1 milligrams q.i.d. The patient did not smoke after the first day although he had been smoking 40 to 50 cigarettes a day prior to that time. The patient expressed the fact that he felt calm, had a dry mouth, and that cigarette smoke tasted terrible to him. The program at the same dosage was finished in one month. The patient lost some weight and felt excellent.

EXAMPLE III

A patient smoked 40 to 50 cigarettes a day. Medication of Example II was prescribed and smoking was reduced to 3 cigarettes the next day with no cigarettes after a one-week period. There was a weight loss, the patient gave up cigarette smoking.

There have been other cases where patients after two weeks have cut their cigarette consumption in half. It is estimated that there would be about a 12% failure rate with the medication of this invention when used with large numbers of people. In many cases, cutting of cigarette smoking amount is noted while in the majority of cases, complete stoppage occurs.

It has been observed that at the present time there appears to be about 85% effectiveness in the use of the combination of drugs of this invention. Often it is found that 30% of the patients stop smoking on the first day, another 30% during the first two weeks and 20% by the third week. About 5% of patients appear to need a second month long treatment at later times. These patients on which the combination has been tried are ambulatory patients going about their normal business in their usual habitat. Institutionalization in conjunction with the combination of drugs in this invention may cut down the failure rate considerably. It is observed that patients on the combination of drugs appear calm, most cut down their smoking by day one to at least half of what they were smoking before and all patients lose weight with a thousand calorie balanced proper food diet. Most patients experience a horrible taste when smoking tobacco ranging from terrible to unbearable. The patients notice increased breathing ability, the disappearance of cough, wheeze, emphysema and the like in many cases. Often the return of smell and taste comes back after a week to those 30% that stop within the first day. Dosage rates can vary greatly. The amount of each drug can be titrated to the individual person. For example if fatigue becomes high, the dosage of clonidine hydrochloride can be cut and if sleep is difficult, a tranquilizer or antihistamine can be given.

Some patients wake at odd hours in the night but most manage to go back to sleep without difficulty. Weight loss accompanies discontinuation of smoking or no weight gain occurs with proper diet. This appears to be a major factor among the people who have stopped. Moreover, the combination of drugs is found useful to promote weight loss in individuals.

While the combination of drugs are preferably given orally in separate tablets, a combined tablet containing the two drugs can be used. Other dosage forms such as injection of the drugs may be used but is inconvenient and may require adjustment of the dosage.

While specific amounts, times and materials have been noted above, many variations are possible. For example, longer time periods of medication can be used. Where weight loss is not complete or satisfactory in the one-month period, the combination of drugs can be continued. Shorter time periods than one month can be used but reoccurrence of the smoking habit may occur. Shorter time periods may be possible where the dosage is increased. Increased dosages beyond that necessary to stop smoking are avoided where possible.

What is claimed is:

1. A method of aiding individuals to stop smoking and lose overweight, said method comprising administering to a patient in need thereof a
   combination consisting essentially of a therapeutically effective amount of a 2-imidazoline derivative selected from the group consisting of 2-[2,6-dichlorophenylamino]-2-imidazoline hydrochloride, naphazoline, tetrahydrazoline, oxymetazoline, xylometazoline, tolazoline, antazoline and mixtures thereof, and an anorectic effective amount of an anorectic.

2. A method in accordance with claim 1 wherein said 2-imidazoline derivative is 2-[2,6-dichlorophenylamino]-2 imidazoline hydrochloride.

3. A method in accordance with claim 1 wherein said anorectic is selected from the group consisting of phentermine, chlorophentermine, fenfluramine, benzphetamine, phenmetrazine, phendimetrozine, diethylpropion, phenylpropanolomine and mixtures thereof.

4. A method in accordance with the method of claim 1 wherein said imidazoline derivative is administered by oral ingestion at a dosage rate of from about 0.5 to about 2.4 milligrams a day.

5. A method in accordance with claim 4 wherein said anorectic is phentermine administered by oral ingestion at a dosage rate of from about 15 to 30 milligrams a day.

6. A method in accordance with the method of claim 2 wherein said imidazoline derivative is administered by oral ingestion at a dosage rate of from about 0.5 to about 2.4 milligrams a day.

7. A method in accordance with claim 6 wherein said anorectic is phentermine administered by oral ingestion at a dosage rate of from about 15 to 30 milligrams a day.

8. A method in accordance with claim 3 wherein said anorectic is phentermine.

9. A combination for aiding individuals to stop smoking and lose overweight comprising a therapeutically effective amount of a 2-imidazoline derivative selected from the group consisting of 2-[2,6-dichlorophenylamino]-2-imidazoline hydrochloride, naphazoline, tetrahydrazoline, oxymetazoline, xylometazoline, tolazoline, antazoline and mixtures thereof, and an anorectic effective amount of an anorectic.

10. A combination in accordance with claim 9 wherein said 2-imidazoline derivative is 2-[2,6-dichlorophenylamino]-2 imidazoline hydrochloride.

11. The combination of claim 9 wherein said anorectic is phentermine.

12. The combination of claim 10 wherein said anorectic is phentermine.

13. The combination of claim 10 wherein said imidazoline derivative is administered at a dosage rate of from about 0.5 to about 2.4 milligrams a day along with from about 15 to about 30 milligrams a day of said phentermine.

14. The combination of claim 9 wherein said anorectic is selected from the group consisting of phentermine resin, chlorophentermine, fenfluramine, benzphentamine, phenmetrazine, phendimetrozine, diethylpropion, phenylpropanolamine and mixtures thereof.

* * * * *